(12) United States Patent
Martin

(10) Patent No.: US 10,481,403 B2
(45) Date of Patent: Nov. 19, 2019

(54) CONTACT LENS WITH RETINAL CAMERA

(71) Applicant: Spy Eye, LLC, Los Gatos, CA (US)

(72) Inventor: Paul Scott Martin, Palo Alto, CA (US)

(73) Assignee: Tectus Corporation, Saratoga, CA (US)

( * ) Notice: Subject to any disclaimer, the term of this patent is extended or adjusted under 35 U.S.C. 154(b) by 0 days.

(21) Appl. No.: 15/898,157

(22) Filed: Feb. 15, 2018

(65) Prior Publication Data

US 2019/0250413 A1    Aug. 15, 2019

(51) Int. Cl.
| | |
|---|---|
| *G02B 27/01* | (2006.01) |
| *H04N 5/232* | (2006.01) |
| *G02C 7/04* | (2006.01) |
| *A61B 3/113* | (2006.01) |

(52) U.S. Cl.
CPC ....... *G02B 27/0179* (2013.01); *G02B 27/017* (2013.01); *G02B 27/0172* (2013.01); *G02C 7/049* (2013.01); *H04N 5/23293* (2013.01); *A61B 3/113* (2013.01); *G02B 2027/014* (2013.01); *G02B 2027/0138* (2013.01); *G02B 2027/0187* (2013.01); *G09G 2380/02* (2013.01)

(58) Field of Classification Search
CPC ............ G02B 27/0179; G02B 27/0172; G02B 2027/0138; G02B 2027/014; G02B 2027/0187; G02B 27/017; A61B 3/113; H04N 5/23293; G09G 2380/02; G02C 7/049; G02C 7/04
See application file for complete search history.

(56) References Cited

U.S. PATENT DOCUMENTS

| | | | | |
|---|---|---|---|---|
| 4,955,711 A | * | 9/1990 | Wise | A01K 37/00 119/715 |
| 9,870,060 B2 | * | 1/2018 | Marggraff | G06F 3/017 |
| 9,939,658 B1 | * | 4/2018 | Gutierrez | G02C 7/083 |
| 10,353,205 B2 | * | 7/2019 | Miller | G03B 21/00 |

(Continued)

FOREIGN PATENT DOCUMENTS

WO    WO 02/31577 A1    4/2002

OTHER PUBLICATIONS

Van De Kraats, "The Pathways of Light Measured in Fundus Reflectometry," Vision Res., 1996, pp. 2229-2247, vol. 36, No. 15.

*Primary Examiner* — Cara E Rakowski
*Assistant Examiner* — Magda Cruz
(74) *Attorney, Agent, or Firm* — Fenwick & West LLP

(57) ABSTRACT

A contact lens contains an inward pointing camera, which will be referred to as a retinal camera since it images light reflected from the retina. These can be reflections of physical features of the retina, of images of an external scene imaged by the eye onto the retina, or images projected onto the retina for example from small projectors contained in the contact lens (femtoprojectors). The field of view (FOV) of the retinal camera is sufficiently large that these reflections can be tracked relative to each other and/or relative to their position within the retinal camera's FOV. This information can be processed to track eye gaze and movement relative to the outside world, to align images from the femtoprojector with the eye and/or to align images from the femtoprojector with images from the outside world, among other tasks.

17 Claims, 11 Drawing Sheets

(56) References Cited

U.S. PATENT DOCUMENTS

| | | | |
|---|---|---|---|
| 2002/0101568 A1* | 8/2002 | Eberl | G02B 27/017 351/211 |
| 2014/0098226 A1* | 4/2014 | Pletcher | H04N 7/18 348/143 |
| 2015/0312560 A1* | 10/2015 | Deering | G02B 13/0085 345/1.3 |
| 2015/0362753 A1* | 12/2015 | Pletcher | G02C 7/083 351/159.03 |
| 2016/0097940 A1* | 4/2016 | Sako | G02C 7/101 351/158 |
| 2016/0103338 A1* | 4/2016 | Hart | G02C 11/10 351/206 |
| 2016/0259406 A1* | 9/2016 | Du | G06F 3/013 |
| 2018/0017814 A1* | 1/2018 | Tuan | G02C 11/10 |
| 2018/0120568 A1* | 5/2018 | Miller | G02C 7/086 |
| 2019/0050643 A1* | 2/2019 | Ulman | G06K 9/209 |

\* cited by examiner

CONTACT LENS WITH RETINAL CAMERA

BACKGROUND

1. Technical Field

This disclosure relates generally to contact lenses that contain a camera that images light reflected from the retina, including contact lenses that function as displays.

2. Description of Related Art

Technologies such as magnetometers and accelerometers form the common basis of modern navigation and tracking systems. However, these systems are prone to errors that make them less viable for use in eye tracking applications. For example, local magnetic materials, such as motor electromagnets and iron in building materials and rocks, can disrupt magnetometer measurements. Similarly, accelerometers can record drift errors that make long time accumulation of travel distance challenging.

Furthermore, most of these systems are fairly large. It can be challenging to reduce the size and power requirements of these systems to meet the requirements of certain eye-tracking or eye-based applications.

BRIEF DESCRIPTION OF THE DRAWINGS

Embodiments of the disclosure have other advantages and features which will be more readily apparent from the following detailed description and the appended claims, when taken in conjunction with the examples in the accompanying drawings, in which:

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

A contact lens contains an inward pointing camera, which will be referred to as a retinal camera since it images light reflected from the retina. These can be reflections of physical features of the retina, of images of an external scene imaged by the eye onto the retina, or images projected onto the retina for example from small projectors contained in the contact lens (femtoprojectors). The field of view (FOV) of the retinal camera is sufficiently large that these reflections can be tracked relative to each other and/or relative to their position within the retinal camera's FOV. This information can be processed to track eye movement relative to the outside world, to align images from the femtoprojector with the eye and/or to align images from the femtoprojector with images from the outside world, among other tasks.

Figure 1:
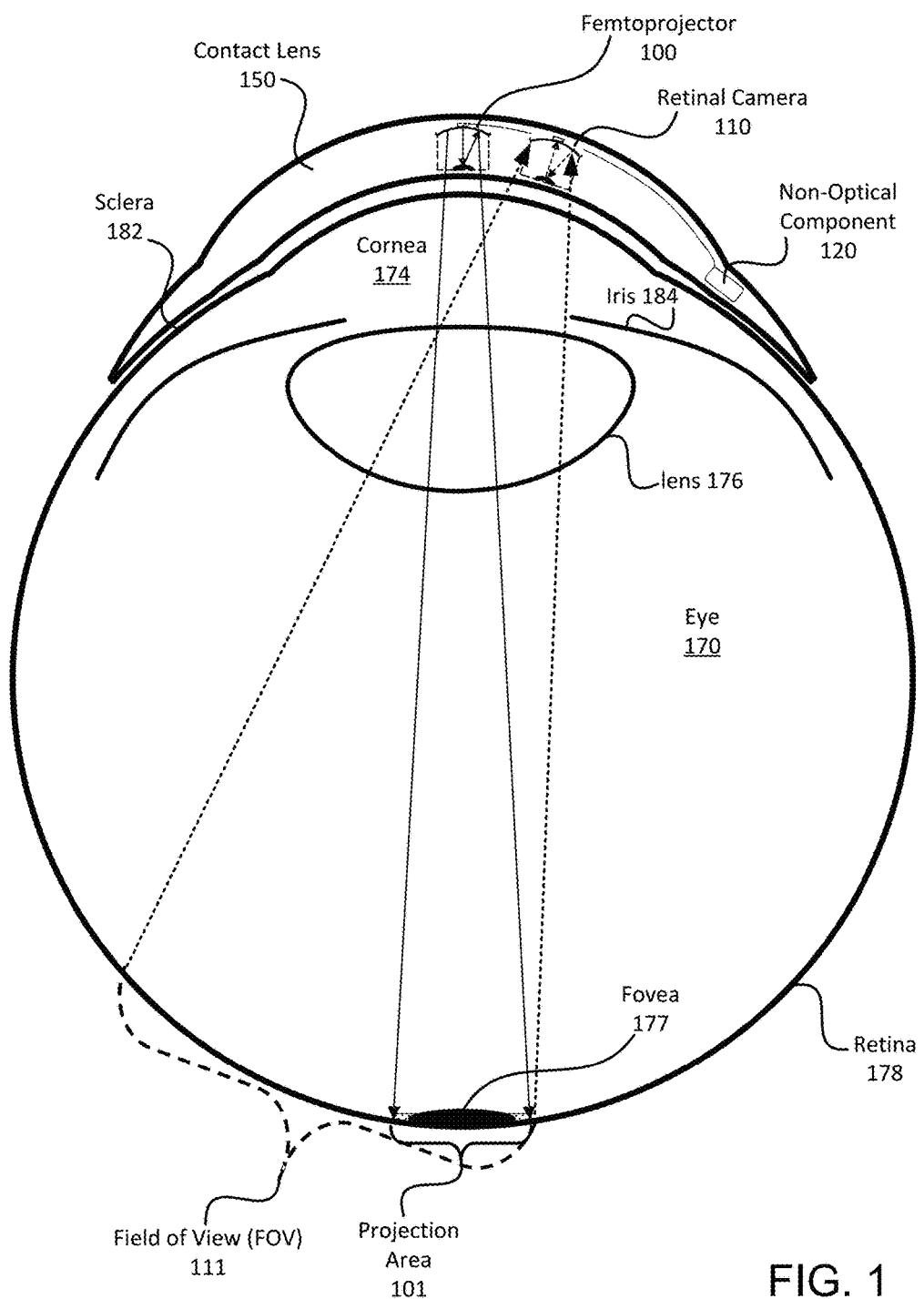
FIG. 1 is a cross-sectional view of a contact lens with retinal camera mounted on a human eye, according to an embodiment.

FIG. 1 is a cross-sectional view of a contact lens with retinal camera mounted on a human eye, according to an embodiment. For reference, FIG. 1 shows the cornea 174, fovea 177, crystalline lens 176, retina 178, sclera 182, and iris 184 of the eye. The contact lens 150 contains various components, including a femtoprojector 100, a retinal camera 110, and a non-optical component 120 (e.g., electronics). The femtoprojector 100 and retinal camera 110 are pointing towards the retina 178. The femtoprojector 100 projects images onto the retina 178 within a projection area 101. The retinal camera 110 images light reflected from the retina 178 within its field of view (FOV) 111. In this example, the non-optical component 120 is located outside the pupil so as to not obstruct light entering the eye 170. In alternative embodiments, different and/or additional components may be included in the contact lens 150. For example, the contact lens 150 may have coils or antennae for transmission of power and data. It may also include other eye tracking technologies, such as gyroscopes, accelerometers, and magnetometers.

In this example, the femtoprojector 100 projects augmented reality images onto the retina 178. The contact lens 150 does not block all light from the external scene (i.e., the outside environment), so some light from the external scene is imaged by the eye onto the retina.

To minimize contact lens 150 movement across the eye when the user blinks or performs daily activities, the contact lens 150 may be a scleral lens that sits on the sclera 182 of the eye. A scleral lens also allows the non-optical component 120 to be contained in portions of the contact lens 150 that do not obscure light that enters the eye 170.

The femtoprojector 100 can project various projections, such as calibration marks or augmented reality (AR) images to be detected by the eye 170. Reflections of these projections from the retina may also be captured by the retinal camera 110 if the projection area 101 overlaps with the FOV 111. The size of femtoprojector 100 can be on the order of a few millimeters to reduce light obscuration. An example femtoprojector 100 is further described with reference to FIG. 2.

The retinal camera 110 captures light reflected from the retina 178. These can be reflections of the external scene, of the projected images from the femtoprojector 100, or of retinal features of the eye 170. The retinal camera 110 has a FOV 111 that is large enough (e.g., 15-30 degrees of arc) that the locations of these reflections relative to each other and/or to the FOV 111 can be determined. This can be done by the non-optical component 120 or by components outside the contact lens. An example retinal camera 110 is further described with reference to FIG. 3.

The location, orientation, and design of the femtoprojector 100 and of the retinal camera 110 determine the location and size of the projection area 101 and of the FOV 111, respectively. These will depend on the intended purpose. For example, the projection area 101 and FOV 111 may each overlap the fovea 177 and with each other, as shown in FIG. 1. In one application, the fovea 177 and projection area 101 are approximately the same size, with the femtoprojector projecting images primarily onto the fovea 177. The FOV 111 is larger and includes both the fovea 177 and the projection area 101. A wider FOV can capture reflections from more of the retina. A narrower FOV produces higher resolution.

Components that do not rely on optical access to the retina are referred to as non-optical components 120. Non-optical components 120 can include electronics that receive image data from the retinal camera 110 and/or transmit projection data to the femtoprojector 100. Based on the image data from the retinal camera 110, the non-optical component can identify and track the relative positions of the reflections. For example, the non-optical component 120 can determine the position of a projected image from the femtoprojector 100 relative to the FOV 111 of the retinal camera 110. In another example, the non-optical component 120 can track eye 170 movement by determining the location of images of the external scene relative to retinal features of the eye 170. In some embodiments, the processing system that performs these functions is not contained entirely within the non-optical component 120 in the contact lens 150. For example, some or all of the processing system can be implemented in remote components that communicate with components 120 in the contact lens 150.

Figure 2A:
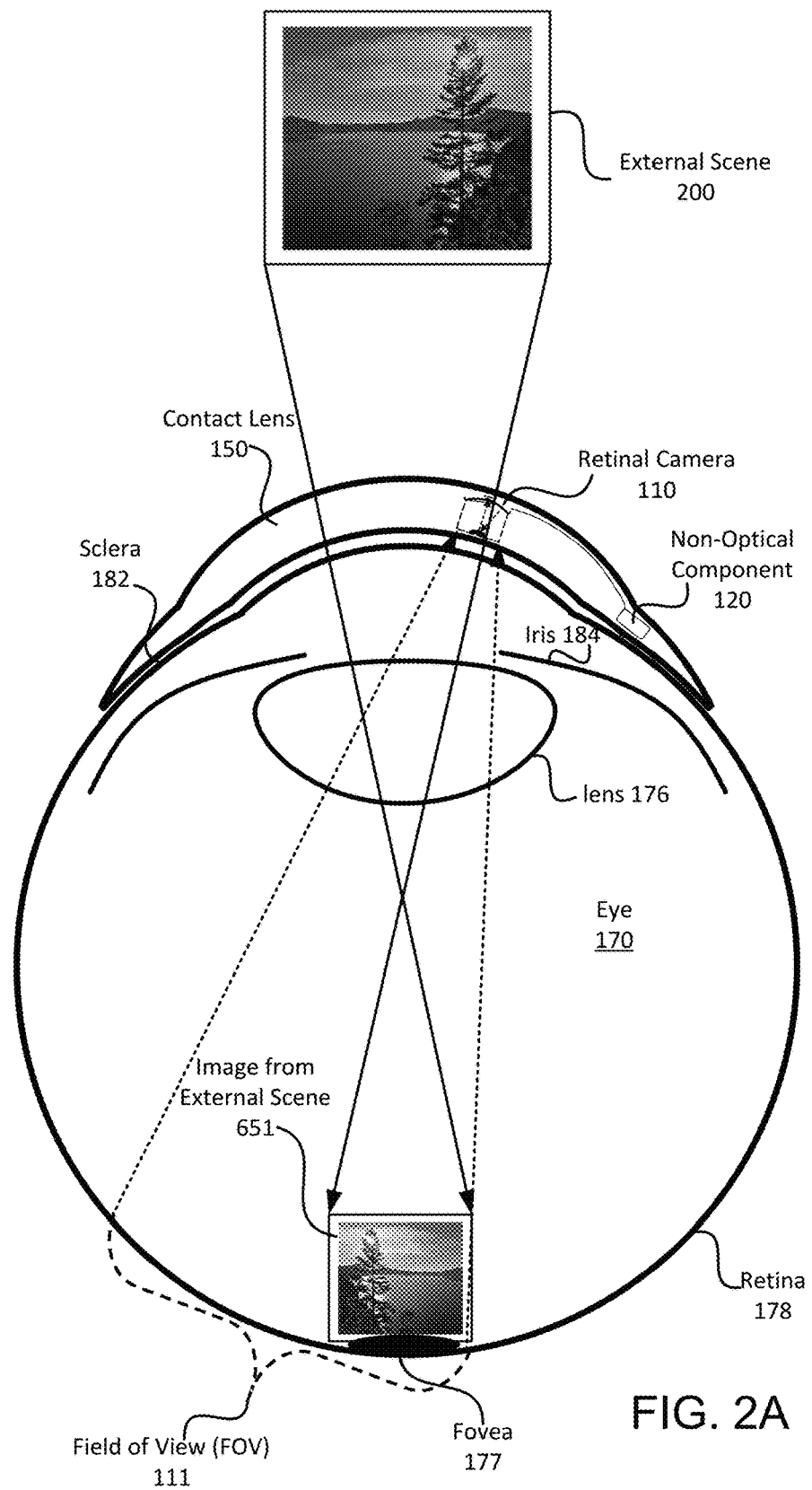
FIG. 2A illustrates imaging of an external scene by the eye, according to an embodiment.
Figure 2B:
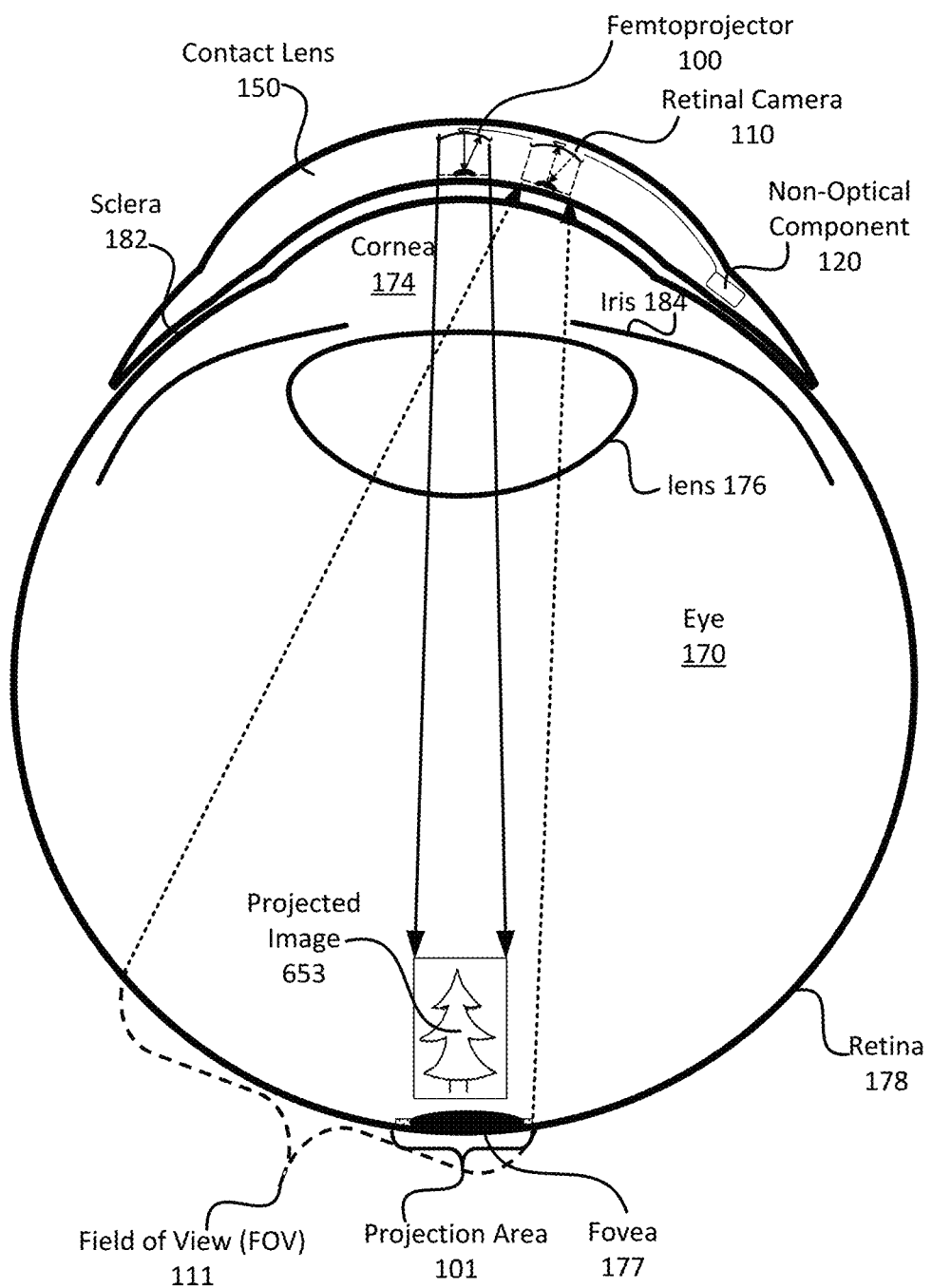
FIG. 2B illustrates projection of an image onto a retina of the eye, according to an embodiment.

FIGS. 2A and 2B illustrate imaging of reflections from the retina 178, according to some embodiments. FIG. 2A illustrates an external scene 200 imaged by the eye onto the retina 178 and image capture of its reflection 651 by a retinal camera 110. For clarity, the femtoprojector of FIG. 1 is not shown. For illustrative purposes, the external scene 200 is a picture of a tree by a lake, with the sun in the background. For example, the user may be viewing this scene 200. The scene 200 is viewed by the eye 170, creating an image 651 on the retina 178. In this example, the image 651 falls on the fovea 177. Some of the light that enters the eye is reflected from the retina 178. The portion of the reflection from the image 651 that is within the retinal camera's FOV is captured by the retinal camera 110. This is one type of reflection that can be captured by the retinal camera 110.

FIG. 2B includes a femtoprojector 100. In this figure, the femtoprojector 100 projects an image 653 onto the retina 178. For illustrative purposes, the projected image 653 includes a tree and the image is projected onto a projection area 101 within the fovea 177. Some of the light is reflected from the retina 178 and captured by the retinal camera 110. This is another type of reflection that can be captured by the retinal camera 110.

If the contact lens is partially transmitting, then both the image 651 of the external scene and the projected image 653 may fall within the FOV 111. The retinal camera 110 captures an image that includes reflections of both the external scene 651 and the projected image 651. It may also capture reflections of retinal features of the eye, such as blood vessels. For purposes of clarity, some of the inversions in the imaging and reflections are ignored.

Figure 3:
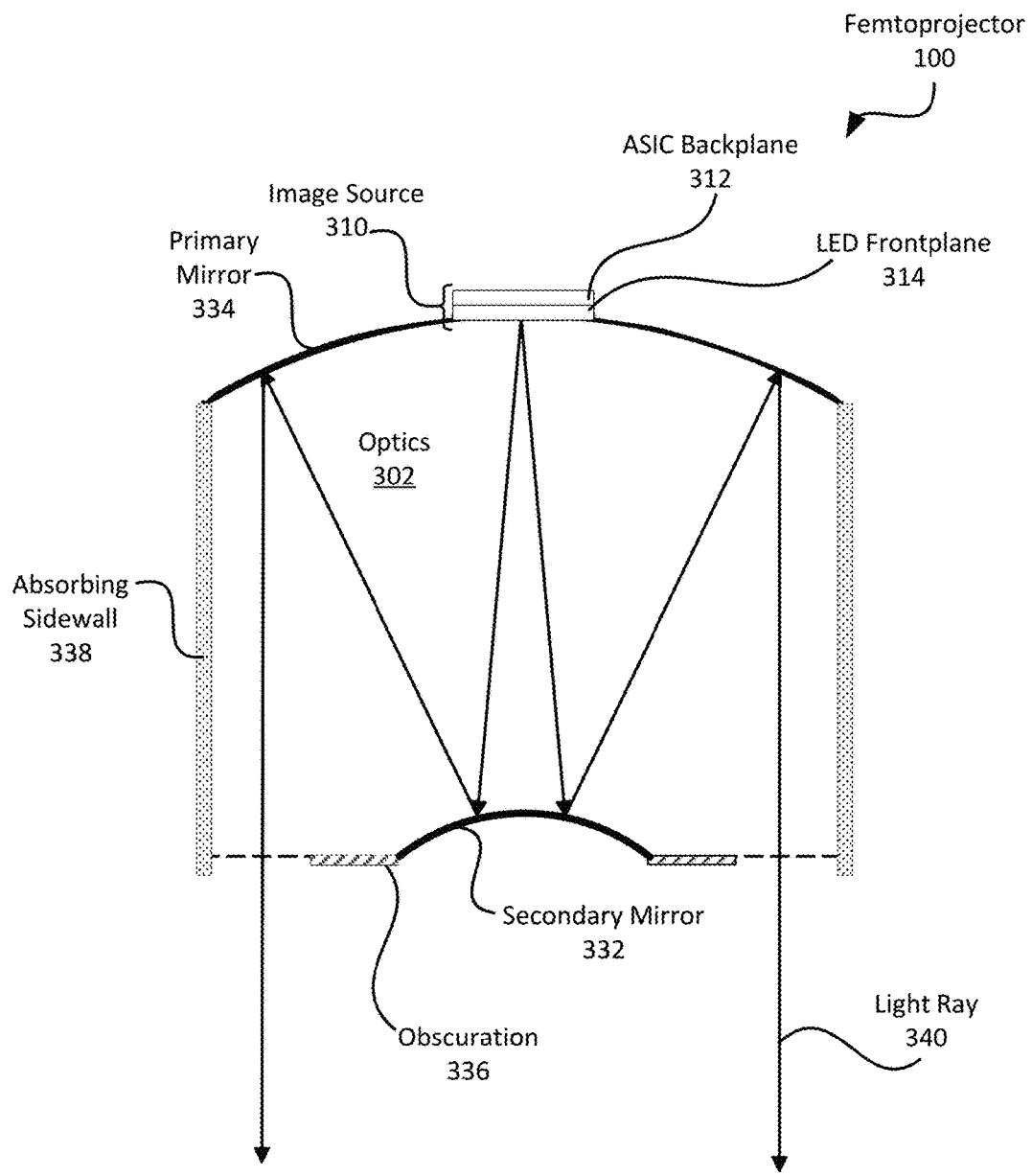
FIG. 3 is a cross-sectional view of a femtoprojector, according to an embodiment.

FIG. 3 is a cross-sectional view of a femtoprojector 100, according to an embodiment. The femtoprojector 100 includes an image source 310 containing an emissive LED frontplane 314 and an application specific integrated circuit (ASIC) backplane 312. The ASIC backplane 312 receives image data and transmits electrical signals to the LED frontplane 314. Light emitted from the image source 310 is projected by the optics 302 to the retina 178. In this design, the optics 302 includes a primary mirror 334 and a secondary mirror 332. An absorbing sidewall 338 and obscuration 336 reduce stray light. This is just one example of a femtoprojector design.

Figure 4:
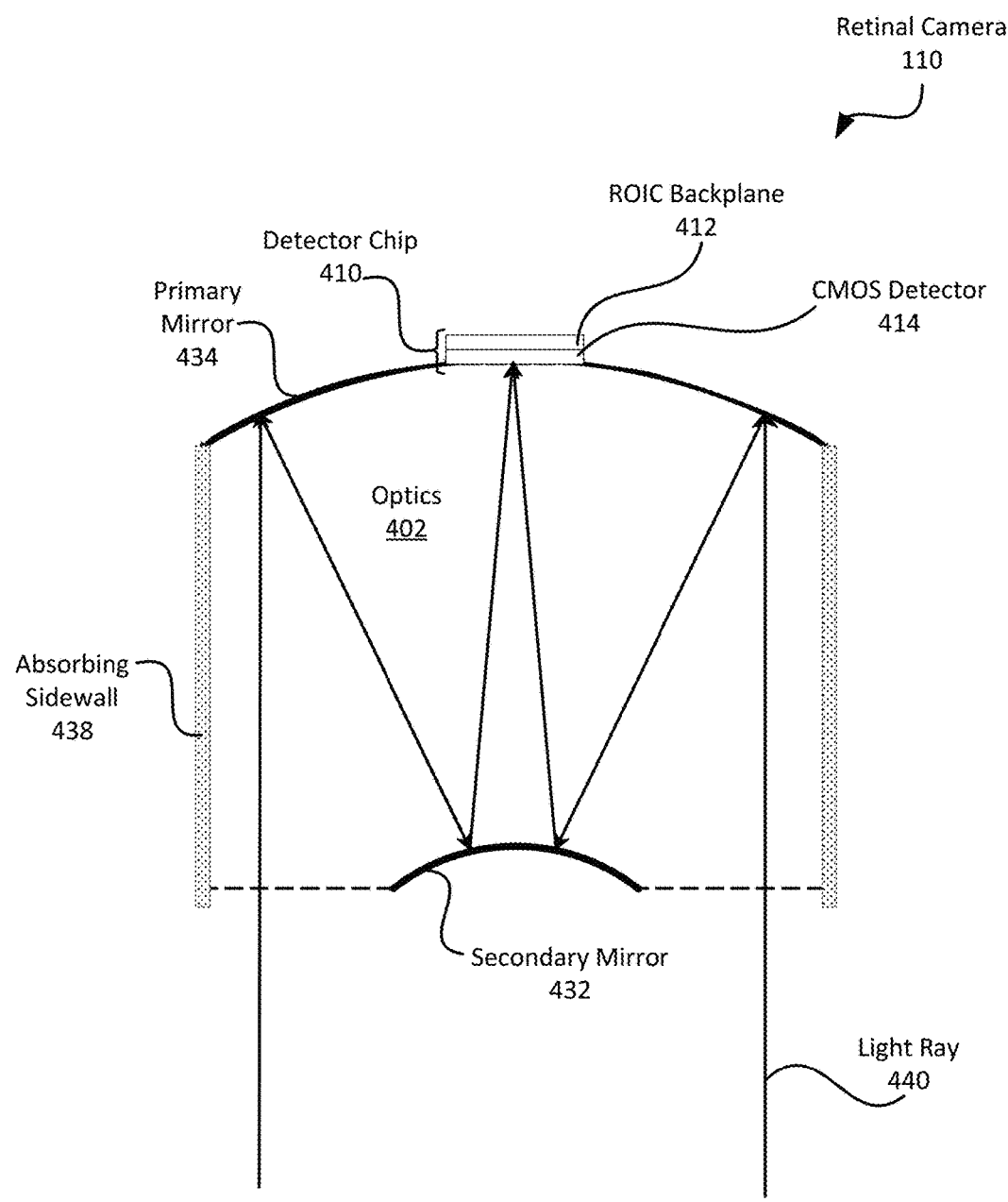
FIG. 4 is a cross-sectional view of a retinal camera, according to an embodiment.

FIG. 4 is a cross-sectional view of a retinal camera 110, according to an embodiment. The retinal camera 110 includes a detector chip 410 containing a photon detector, such as a CMOS detector 414, and a read out integrated circuit (ROIC) 412. Light rays 440 reflected from the retina 178 are accepted into the optics 402. The primary mirror 434 and secondary mirror 432 image the reflected light rays 440 onto the CMOS detector 414. At a prescribed frequency, such as 30-240 Hz, the ROIC 412 reads the image from the CMOS detector 414 and transmits the data to electronics 120. This is just one example of a design for a retinal camera. For example, other designs can be based on lens rather than mirrors.

Figure 5:
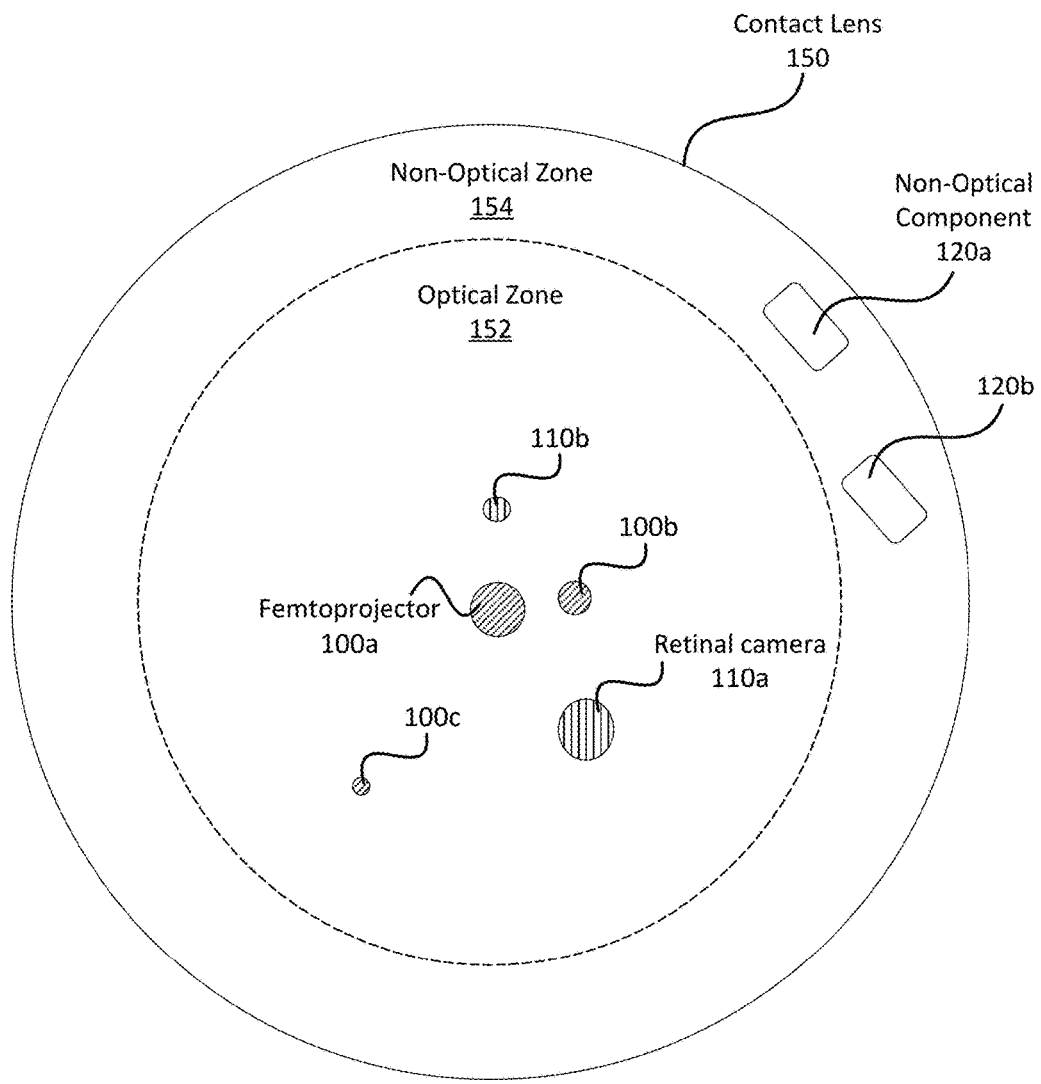
FIG. 5 is a plan view of a contact lens, according to an embodiment.

FIG. 5 is a plan view of a contact lens 150, according to an embodiment. The contact lens 150 can be divided into an optical zone 152 and a non-optical zone 154. The optical zone 152 (in front of the pupil) contains femtoprojector(s) 100a-c and retinal camera(s) 110a-b. The femtoprojectors 100 and retinal cameras 110 can cover different regions of the retina 178. For example, one femtoprojector 100 might project higher resolution images to the fovea 177, while another femtoprojector 100 projects lower resolution images to peripheral regions of the retina. The non-optical zone 154 can contain non-optical components 120a-b.

Figure 6A:
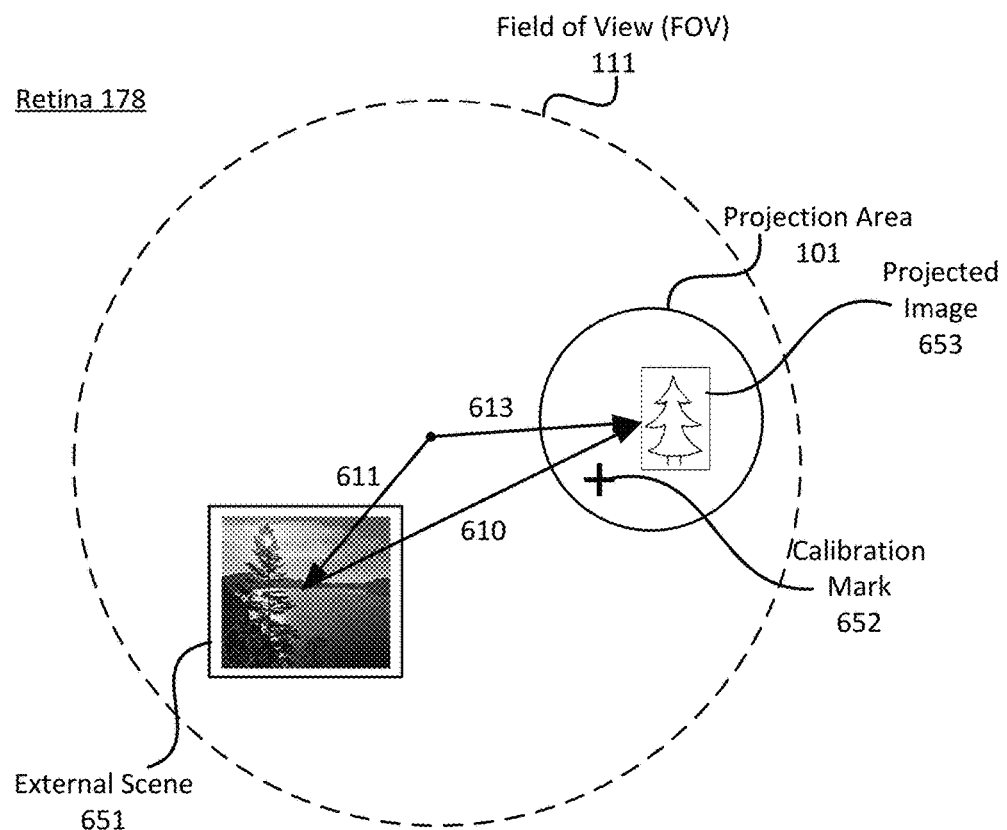
FIGS. 6A-6D illustrate relative positioning of reflections from the retina, according to embodiments.

FIG. 6A illustrates relative positioning of reflections from the retina, according to an embodiment. This figure shows the surface of the retina with reflections of the external scene 651. Bright objects in the external scene, such as incandescent bulbs, the sun, street lamps, and the moon, may be especially useful in the following applications. In some cases, bright objects may be intentionally introduced to the external scene. FIG. 6A also shows reflections of a projected image 653 and a calibration mark 652 (which is a special type of projected image). The projection area 101, which is the extent of the image created by the femtoprojector, is also marked on FIG. 6A. The calibration mark 652 (or other projected images) could be made not visible to the human if they are projected at non-visible wavelengths and the retinal camera also operates at those wavelengths. In FIG. 6A, the external scene 651 and projection area 101 are shown as non-overlapping. This is done for clarity. The two areas may or may not overlap.

FIG. 6A also shows the FOV 111 of the retinal camera. In this example, all of the reflections fall within the FOV, so the retinal camera will capture all of these reflections. From the captured image(s), the position of each reflection relative to the camera FOV will be known and the position of different reflections relative to each other can be calculated. These may also be tracked over time. This relative position information can be used to adjust the location of the projected images 652,653 or possibly of the projection area 101.

For example, this relative position information may be used to locate the projected image 652,653 or the projection area 101 relative to the external scene 651. This relative position is represented in FIG. 6A by the vector 610. It may be useful just to know the relative positioning 610. For example, the distance between the projected tree 653 and the real tree 651 is calculated, or the change in distance over time (i.e., the speed) between a projected football and a real person is calculated. Alternately, the relative positioning 610 may be used as feedback to adjust the positioning. For example, the projected tree 653 is supposed to be 10 meters to the right of the real tree 651 and, based on the calculated relative position 610, the projected tree 653 can be moved within the projection area 101 so as to maintain that position relative to the real tree 651. In many augmented reality applications, it is desirable to position projected images 653 relative to real world objects 651. The reflected images shown in FIG. 6A allow a direct measure of those relative positions 610. As another example, the calibration mark 652 may be aligned to a bright spot in the external scene 651 or to a calibration object placed into the external scene 651.

Calculation of vector 610 based on the captured images 651 and 652,653 is a direct measurement of the relative position 610. This relative position 610 can also be determined indirectly. Perhaps the retinal camera captures only the reflection 651 of the external scene. Maybe the projected image is too dim or turned off or even outside the FOV 111. In this case, the relative position of the external scene 651 within the FOV 111 can be determined from the captured image. This is represented by vector 611 in FIG. 6A, which extends from the center of the FOV 111 to the external scene 651. The position of the projection area 101 relative to the FOV 111 may be known by other methods, for example because the physical layout of the femtoprojector and retinal camera within the contact lens is known. This is represented by vector 613 in FIG. 6A. The two relative positions 611 and 613 can be combined to calculate the relative positioning of the external scene 651 and the projected image 653.

Figure 6B:
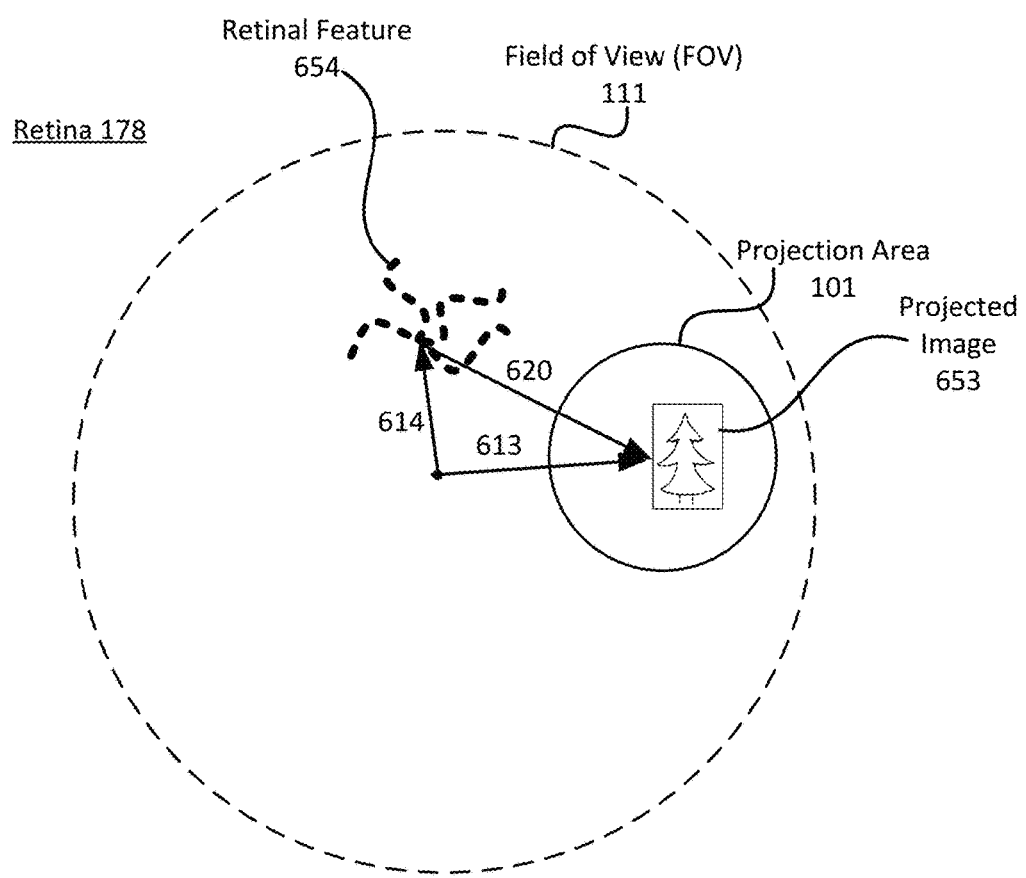

FIG. 6B is similar to FIG. 6A, but showing a reflection 653 from the projected image and a reflection 654 from a retinal feature, according to an embodiment. The retinal feature 654 is a distinctive feature on the retina 178 that can be used as a reference location for the eye 170 itself. Examples retinal features 654 include the fovea 177, the optic nerve, and patterns of blood vessels. The retinal feature 654 may be detected within the captured image using pattern recognition. Any number of retinal features 654 can be detected.

In this example, relative position information may be used to locate the projected image 653 or the projection area 101 relative to the retina. This relative position is represented in FIG. 6B by the vector 620. For example, it may be desired that the femtoprojector projects its images to the fovea, so that the projection area 101 is centered on the fovea, and the fovea is located relative to the retinal feature 654. The reflected images shown in FIG. 6B allow a direct measure of the relative position 620 between the projected image 653 and the retinal feature 654.

This relative position 620 can also be determined indirectly. For example, if the retinal feature 654 is within the FOV 111, then the relative position of the retinal feature 654 within the FOV 111 can be determined from the captured image. This is represented by vector 614 in FIG. 6B. The relative position 613 of the projection area 101 relative to the FOV 111 may be known by other methods. The two relative positions 614 and 613 can be combined to calculate the relative positioning of the eye 654 and the projected image 653.

Alternately, perhaps only the projected image 653 is captured, then the relative position 613 of the projection area 101 relative to the FOV 111 can be determined from the captured image. However, the relative position 614 between the FOV 111 and the eye may be known, for example the retinal feature 654 may be the fovea, and the scleral contact lens system may be designed so that the FOV 111 is centered on the fovea. Regardless of how obtained, the two relative positions 614 and 613 can be combined to calculate the relative positioning of the eye 654 and the projected image 653.

Figure 6C:
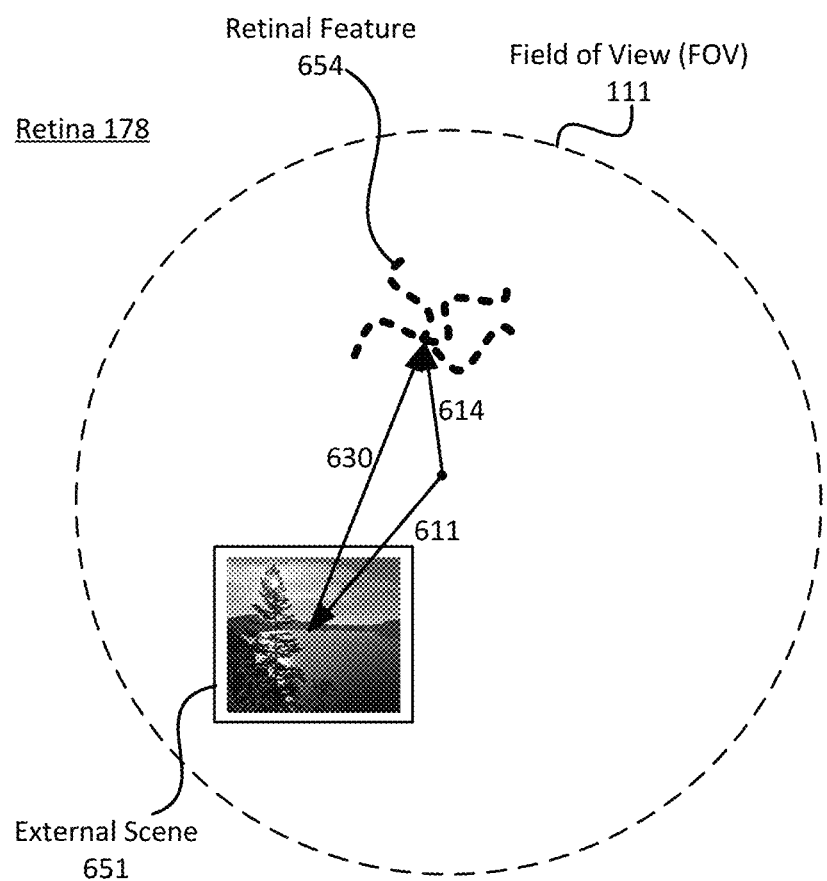

FIG. 6C shows reflections of the external scene 651 and retinal feature 654. The vectors 611, 614 show relative positions of each reflection within the FOV 111. These can be determined directly if the reflections are captured by the retinal camera. In FIG. 6C, it is desired to implement eye tracking, i.e., to track the gaze direction and/or position of the eye relative to an external reference frame. Eye tracking may be achieved by determining the relative motion between a stationary external scene 651 along the retina, e.g. relative to retinal feature 654. Changes in position on the retina can indicate rotation of the eye. Changes in the relative size of the external scene 651 can be used to measure changes in distance between the user and the external scene. For example, if the image from the external scene 651 becomes smaller, the distance between the user and the external scene may be increasing. These methods can be used to determine eye tracking that includes eye focus, angle, and velocity.

To track the eye's gaze direction, the image of the external scene 651 captured by the retinal camera may be lower quality than is required for imaging purposes. Preferably, the object tracked in the external scene 651 is a bright stationary object, such as a light bulb.

Eye tracking may be achieved by directly calculating the relative position 630 from a captured image containing both the external scene 651 and an eye reference 654. It can also be calculated indirectly, for example by combining relative positions 611 and 614 where relative position 611 is determined from the captured image and relative position 614 is otherwise known. In FIG. 6C, there is no projected image and eye tracking can be implemented in contact lenses without femtoprojectors.

Figure 6D:
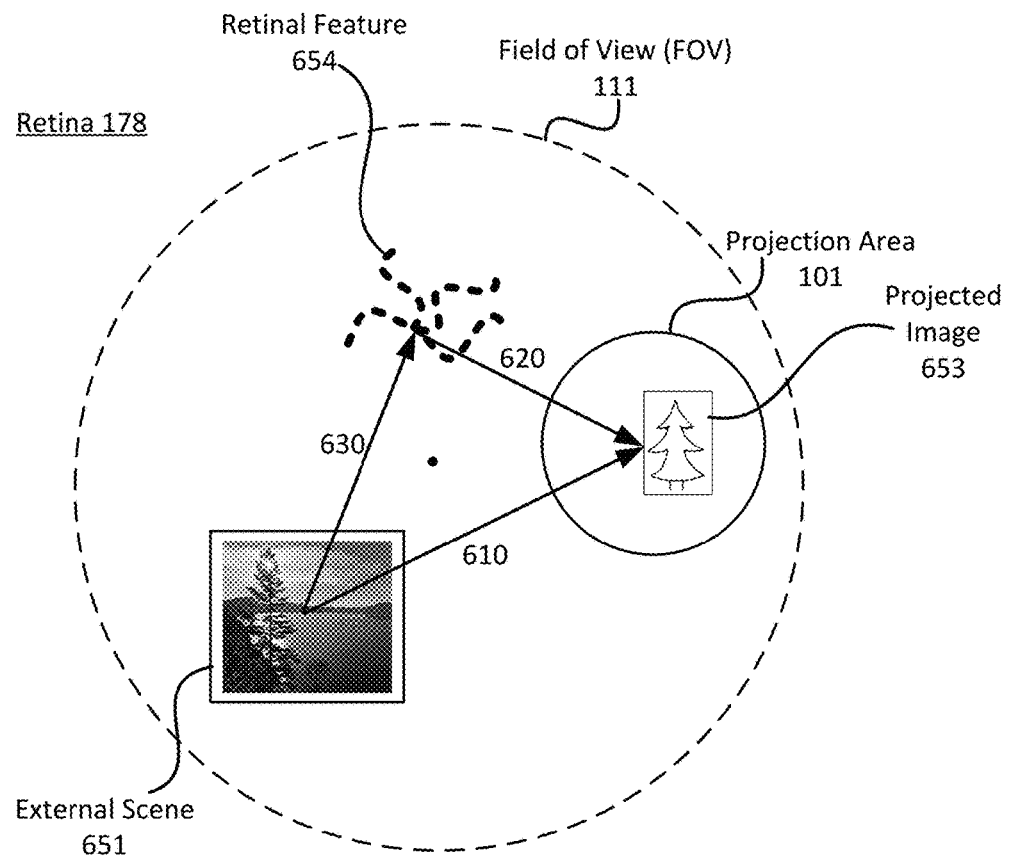

As a final example shown in FIG. 6D, the relative position 630 can be determined from relative positions 610 (determined from the captured image) and 620 (known from other methods).

The operations described above can be performed during real-time operation, for example to register augmented reality objects with the real world scene. Alternatively, they may be used for calibration, for example to align the femtoprojector on the fovea or to calibrate deviations from the desired position. In another aspect, they can be based on single captured images, multiple images captured over time or differences in images captured over time.

Figure 7:
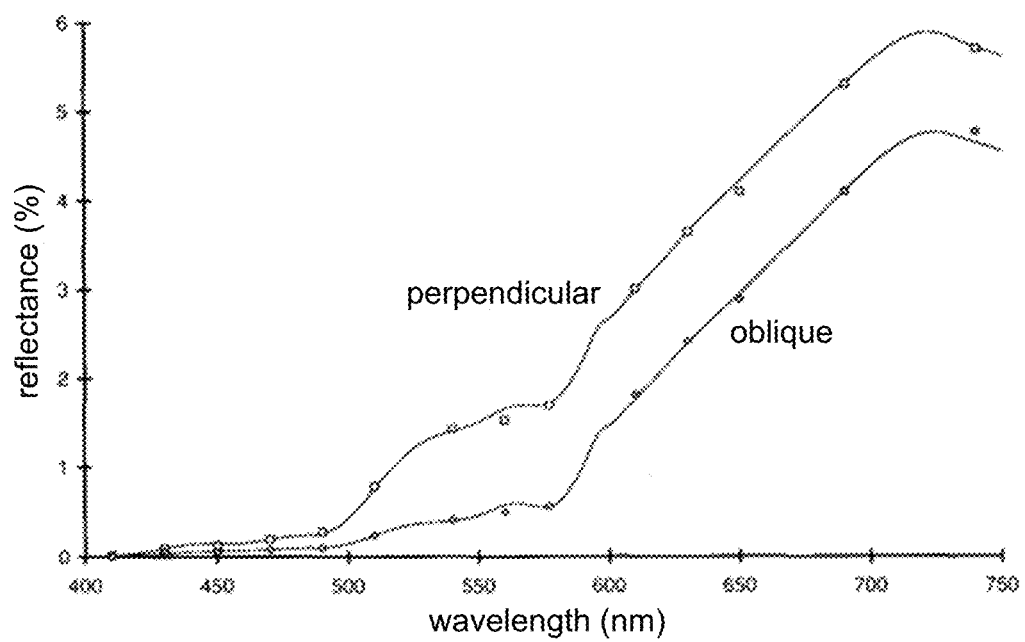
FIG. 7 (prior art) is a graph of the reflectivity of a human retina, according to an embodiment.

FIG. 7 (prior art) is a graph of the reflectivity of a human retina 178. The graph is from "The Pathways of Light Measured in Fundus Reflectometry," Jan van de Kraats, Vision Res., Volt 36, No. 15 pp 2229-2247, 1996. Note that perpendicular reflectance varies from ~0.1% at 450 nm (Blue) to ~5% at 680 nm (Deep Red). These reflections are captured by the retinal camera 110.

Although the detailed description contains many specifics, these should not be construed as limiting the scope of the invention but merely as illustrating different examples and aspects of the invention. It should be appreciated that the scope of the invention includes other embodiments not discussed in detail above. For example, the contact lens devices described above can be used with animals, as well as with humans. Various other modifications, changes, and variations which will be apparent to those skilled in the art may be made in the arrangement, operation, and details of the method and apparatus of the present invention disclosed herein without departing from the spirit and scope of the invention as defined in the appended claims. Therefore, the scope of the invention should be determined by the appended claims and their legal equivalents.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

What is claimed is:

1. A system comprising:
an eye-mounted device comprising:
a scleral contact lens that sits on a sclera of a wearer's eye; and
a retinal camera contained in the scleral contact lens, the retinal camera imaging light reflected from a retina of a wearer of the scleral contact lens, the reflected light imaged by the retinal camera comprising a reflection of an external scene imaged by the eye onto the retina; and
a processing system that determines a gaze direction of the eye relative to the external scene based on the reflected light imaged by the retinal camera.

2. The system of claim 1 where:
the reflected light imaged by the retinal camera further comprises a reflection of retinal features of the eye; and
the processing system determines the gaze direction based on a relative positioning between the reflection of the retinal features and the reflection of the external scene.

3. The system of claim 1 where:
the processing system determines the gaze direction based (a) on a location of the reflection of the external scene within a field of view of the retinal camera, and also (b) on a known location of the field of view of the retinal camera on the retina of the eye.

4. The system of claim 1 further comprising:
a femtoprojector also contained in the scleral contact lens, the femtoprojector performing a projection of images onto a projection area on the retina;
where:
the reflected light imaged by the retinal camera further comprises a reflection of the projected image; and
the processing system determines the gaze direction based (a) on a relative positioning between the reflection of the external scene and the reflection of the projected image, and also (b) on a known location of the projected image on the retina of the eye.

5. The system of claim 1 further comprising:
a femtoprojector also contained in the scleral contact lens, the femtoprojector performing a projection of images onto a projection area on the retina, where a location of an object in the projected image depends on the gaze direction.

6. The system of claim 1 where the retinal camera images a sequence of frames of light reflected from the retina; and the processing system determines the gaze direction based on temporal differences between different frames.

7. The system of claim 1 where the gaze direction is used in real-time operation of the eye-mounted device.

8. The system of claim 1 further comprising:
a femtoprojector also contained in the scleral contact lens, the femtoprojector performing a projection of images onto a projection area on the retina.

9. The system of claim 8 further comprising:
a processing system that determines a relative positioning based on the reflected light imaged by the retinal camera, the relative positioning used to determine a location of the projection.

10. The system of claim 9 where the relative positioning is used to determine the location of the projection on the retina.

11. The system of claim 10 where:
the reflected light imaged by the retinal camera comprises a reflection of the projected image and a reflection of retinal features of the eye;
the relative positioning determined by the processing system is relative positioning between the reflection of the projected image and the reflection of the retinal features; and
the location of the projection on the retina is determined based on the relative positioning.

12. The system of claim 10 where:
the reflected light imaged by the retinal camera comprises a reflection of retinal features of the eye;
the relative positioning determined by the processing system is a location of the reflection of the retinal features within the field of view of the retinal camera; and
the location of the projection on the retina is determined based (a) on a known location of the projection area relative to a field of view of the retinal camera, and also (b) on the location of the reflection of the retinal features within the field of view of the retinal camera.

13. The system of claim 10 where:
the reflected light imaged by the retinal camera comprises a reflection of the projected image;
the relative positioning determined by the processing system is a location of the reflection of the projected image within a field of view of the retinal camera; and
the location of the projection on the retina is determined based (a) on the location of the reflection of the projected image within a field of view of the retinal camera, and also (b) on a known location of the field of view of the retinal camera on the retina of the eye.

14. The system of claim 9 where the relative positioning is used to determine a location of the projection relative to an external scene imaged by the eye onto the retina.

15. The system of claim 14 where:
the reflected light imaged by the retinal camera comprises a reflection of the projected image and a reflection of the external scene imaged onto the retina;
the relative positioning determined by the processing system is relative positioning between the reflection of the projected image and the reflection of the external scene; and
the location of the projection relative to the external scene is determined based on the relative positioning.

16. The system of claim 14 where:
the reflected light imaged by the retinal camera comprises a reflection of the external scene imaged onto the retina;
the relative positioning determined by the processing system is a location of the reflection of the external scene within the field of view of the retinal camera; and
the location of the projection relative to the external scene is determined based (a) on a known location of the projection area relative to a field of view of the retinal camera, and also (b) on the location of the reflection of the external scene within the field of view of the retinal camera.

17. The system of claim 9 where the femtoprojector projects a calibration image onto the retina; the reflected light imaged by the retinal camera comprises a reflection of the calibration image; and the relative positioning is determined based on a location of the reflection of the calibration image within a field of view of the retinal camera.

* * * * *